United States Patent [19]

Deiner et al.

[11] Patent Number: 4,477,498

[45] Date of Patent: Oct. 16, 1984

[54] PROCESS FOR THE PRODUCTION OF PERFLUOROALKYL RESIDUE CONTAINING CONDENSATION PRODUCTS, THE CONDENSATION PRODUCTS PREPARED ACCORDINGLY, AND THEIR USE

[75] Inventors: Hans Deiner, Neusaess; Franz Mosch, Gessertshausen; Bernhard Sandner; Willy Bernheim, both of Diedorf, all of Fed. Rep. of Germany

[73] Assignee: Ciba-Geigy Corporation, Ardsley, N.Y.

[21] Appl. No.: 408,084

[22] Filed: Aug. 13, 1982

[30] Foreign Application Priority Data

Aug. 22, 1981 [DE] Fed. Rep. of Germany ....... 3133303

[51] Int. Cl.$^3$ .............................................. B05D 3/02
[52] U.S. Cl. .................................. 427/389.9; 427/381; 427/389; 427/392; 427/393.4; 525/509; 528/254; 544/199; 544/200
[58] Field of Search ......................... 525/509; 528/254; 544/199, 200; 427/389, 389.9, 392, 393.4

[56] References Cited

U.S. PATENT DOCUMENTS

| | | |
|---|---|---|
| 3,088,849 | 5/1963 | Friedlander .......................... 428/422 |
| 3,296,264 | 1/1967 | Gagliardi .......................... 260/249.6 |
| 3,320,255 | 5/1967 | Kalas et al. .......................... 260/248 |
| 3,362,782 | 1/1968 | Gagliardi .............................. 8/190 |
| 3,510,455 | 5/1970 | Olson .................................. 528/254 |
| 3,522,084 | 7/1970 | Pittman et al. .................... 427/393.4 |
| 3,894,992 | 7/1975 | Raynolds .......................... 260/249.6 |
| 4,171,415 | 10/1979 | Kleiner et al. .................... 427/393.4 |

FOREIGN PATENT DOCUMENTS

| | | |
|---|---|---|
| 1208745 | 1/1969 | Fed. Rep. of Germany . |
| 2013103 | 10/1971 | Fed. Rep. of Germany . |
| 1768939 | 2/1972 | Fed. Rep. of Germany . |
| 611013 | 10/1948 | United Kingdom . |
| 1019338 | 2/1966 | United Kingdom . |

OTHER PUBLICATIONS

Methoden der organischen chemie (Houben-Weyl), (1955), pp. 42-46.

Primary Examiner—Theodore E. Pertilla
Attorney, Agent, or Firm—Edward McC. Roberts

[57] ABSTRACT

The present invention relates to new condensation products of
(A) 1 mole of a highly etherified hexamethylol melamine and
(B) 3 to 6 moles of a thiol of the formula $$R_f\text{—}X\text{—}SH, \qquad (1)$$

$R_f$ standing for perfluorinated alkyl with 4 to 14 C-atoms and X for divalent ethylene or isopropylene radicals, wherein the components (A) and (B) are reacted under increasing temperature up to at least 145° C. within a period of at least 40 minutes.

In form of their aqueous dispersions, the condensation products are suitable for oil- and water-repellent finishing of fibrous, preferably textile materials.

8 Claims, No Drawings

PROCESS FOR THE PRODUCTION OF PERFLUOROALKYL RESIDUE CONTAINING CONDENSATION PRODUCTS, THE CONDENSATION PRODUCTS PREPARED ACCORDINGLY, AND THEIR USE

The present invention relates to perfluoroalkyl radicals containing condensation products, the process for their manufacture as well as their use in form of aqueous dispersions to achieve oil- and water-repellency on fibrous material, especially on textile material.

U.S. Pat. No. 3,510,455 teaches the production of thermosettable fluorinated prepolymers by reacting an aldehyde, a nitrogen compound, e.g. urea or melamine, and a fluorinated aliphatic compound which contains a perfluorinated alkyl chain as well as at least one functional group with an active hydrogen atom. These prepolymers are soluble in usual solvents and cure on polar surfaces to continuous, adherent films. The reaction takes place in other molar ratios than according to the invention and at average relatively low temperatures (see examples 1 to 16). The thiols (B) are not disclosed. The prepolymers prepared according to prior art are obviously not suitable for the treatment of textile materials.

U.S. Pat. No. 3,362,782 teaches to apply condensation products of optionally etherified methylolated compounds of heterocyclic nitrogen compounds with 1,1-dihydroperfluoroalkyl alcohols or perfluorocarboxylic acid amides, e.g. with perfluoroheptyloxymethylpenta-(methoxymethyl)-melamine for the anti-soiling finishing of cellulose textile material. For the application an organic solvent is used. However, the oil- and water-repellent effects achieved with these condensation products do not meet the present requirements any more. Moreover, unproportionally large quantities of these condensation products have to be used. It has now been found that the inventive condensation products—as described hereinafter—overcome these disadvantages and provide a considerable improvement in the field of oil- and water-repellent finishes of fibrous materials.

Therefore, one object of the present invention are new condensation products of
(A) 1 mole of hexamethylol melamine, highly etherified with $C_1$- to $C_4$-alcohols, and
(B) 3 to 6 moles of a thiol of the formula

wherein $R_f$ is a perfluoroalkyl of 4 to 14 C-atoms and X is the divalent radical of ethylene or isopropylene.

Another object of the present invention is the process for the manufacture of the inventive condensation products which comprises reacting
(A) 1 mole of hexamethylol melamine, highly etherified with $C_1$- to $C_4$-alcohols, and
(B) 3 to 6 moles of a thiol of the formula

wherein $R_f$ is a perfluoroalkyl of 4 to 14 carbon atoms and X is the divalent radical of ethylene or isopropylene,
the reaction temperature being increased to at least 145° C. within a period of at least 40 minutes.

A further object of the present invention is the use of the condensation products in form of their aqueous dispersions for the oil- and water-repellent finishing of fibrous material, especially of textile material.

The condensation products prepared in accordance with the inventive process show oil- and water-repellent properties on fibrous material which are superior to those of the mentioned prior art.

In view of prior art it could not be expected that condensation products of selected starting compounds, viz. the highly etherified hexamethylol melamine (A) and the thiol (B) at a mole ratio of 1:(3 to 6), especially at 1:(4 to 5.5), would show particularly favourable properties with regard to oil- and water-repelling on fibrous materials.

The highly etherified hexamethylol melamines which are used as starting materials are known. They can for example be prepared by the process according to GB-PS No. 611 013. The term highly etherified hexamethylol melamine includes those compounds in which the melamine is completely methylolated and the methylol groups are etherified to a high degree. A very good starting material is for example a hexamethylol melamine ether, the methylol groups of which are etherified to 88 to 95 mole % with an alcohol containing 1 to 4, especially 1 to 3 C-atoms. For economical reasons the corresponding methylether is especially preferred (called hexamethylol melamine hexamethylether hereinafter). The complete methylolation and the high degree of etherification are important because otherwise the melamine derivative (A) is not sufficiently stable for the reaction with the thiol (B).

Also the second starting material (B), the aliphatic thiols containing perfluorinated alkyl radicals of the formula

in which $R_f$ is perfluoroalkyl of 4 to 14 C-atoms and X is the divalent radical of ethylene ($CH_2$—$CH_2$—) or isopropylene (($CH_3$)$_2$C—$CH_2$—), are known U.S. Pat. No. 3,088,849 and German Offenlegungsschrift No. 20 13 103, corresponds to ZA-application 71 01 739). Their manufacture is carried out by reaction of perfluoroalkylhalides with thiourea and subsequent saponification with alkali or aqueous solution of ammonia. For practical reasons those thiols (B) are preferred in which X is the divalent ethylene radical (—$CH_2CH_2$—).

Due to the fact that the resulting condensation products of the highly etherified hexamethylol melamine (A) and the thiol (B), are used for oil- and water-repellent finishing of fibrous material, especially of textile material, those thiols are preferred for the preparation in which the perfluorinated alkyl has at least 6 C-atoms. It is not necessary that compound (B) is a pure form. Preferably even technical mixtures can be applied in which the perfluorinated alkyl residue mainly contains 6,8 to 10 C-atoms, that means 7 to 9 C-atoms on the average.

The mole ratio of (A) to (B) for the manufacture of the condensation products is 1:(3 to 6), especially 1:(4 to 5.5). It is clearly possible to work with a surplus of compound (B). This has to be removed, however, at the end of the reaction, if necessary under reduced pressure.

Condensation is carried out by mixing the two components in the required mole ratio and reacting them together while stirring e.g. in a 4-neck-round-bottom-flask, equipped with a stirrer, a gas inlet tube, an internal thermometer and a descending condenser, appropriately in a protective gas atmosphere, increasing the temperature to at least 145° C. within a period of at least 40 minutes. Preferably the temperature is increased step by step, that is that within about 15 to 45 minutes the temperature is increased up to 95° to 130° C. in the steadiest possible manner, then within further 25 to 120 minutes, especially 60 to 120 minutes, increased up to 145° to 200° C., especially to 160° to 180° C. It is of advantage to keep this temperature for further 2 to 6 hours to complete the reaction. During the condensation process the slightly volatile alcohol is removed by distillation. The yield, controlled by reweighing of the flask which has been tared before, amounts to about 92 to 98% by weight of the theory.

In case that the last phase of the heating process has been carried out at temperatures below 145° C. the obtained condensation products will prove still sufficient oil-repellent effects, the water-repellent effects, however, are not satisfying.

The reaction can be carried out in the presence of a reetherification catalyst, especially of an acid catalyst. Heavyly volatile inorganic or organic acids such as phosphoric acid, p-toluenesulphonic acid or oxalic acid in quantities of 0.05 to 0.5, especially of 0.1 to 0.25% by weight, referred to the total reacting mixture, are suitable for this purpose. In principle it is also possible to carry out the reaction in a solvent which shows a sufficiently high boiling point.

After heating and cooling to about 70° to 90° C. the condensation product is dissolved in a suitable solvent of slightly higher temperatures, its amount being about three times the weight of the condensation product. The resulting reaction products are insoluble in common organic solvents at normal temperatures, they can easily be converted, however, into stable, aqueous emulsions in form of their solutions in fluorinated hydrocarbons such as 1,1,2-trichloro-1,2,2-trifluoro ethane, benzotrifluoride or 1,3-bis (trifluoromethyl)-benzene in usual manner by the aid of emulsifiers.

The emulsifiers are known. For example, the following can be applied:

polyvinylalcohol in aqueous solution, ethoxylated fatty acid amides, ethoxylated fatty acid, ethoxylated fatty alcohols and ethoxylated fatty amines, latter also in form of their salts with low molecular organic acid or mineral acids, as well as quaternary ammonium compounds, as octadecyloxymethylpyridinium chloride or cetyldimethylbenzylammoniumchloride. Suitable emulsifiers are also reaction products of epoxides and di- or polyamines such as described in U.S. Pat. No. 3,320,197, or condensation products of urea or its derivatives with epoxides and selected amines as described in U.S. Pat. No. 3,729,437.

The emulsifiers can be applied in a usual ratio of 3 to 40, especially 8 to 25% by weight (calculated as solid substance), based on the weight of the condensation product that is free of solvent.

It is useful to remove the solvent after emulsification by methods already known because this avoids pollution of the air by solvent vapour when applying the product and, furthermore, the removed solvent can be used again.

In general the aqueous dispersions can be combined with finishing agents known in the textile industries. Preferred are e.g. agents which improve crease resistance. For further improvement, especially with regard to water-repellent effects, the condensation products according to the invention are preferably applied together with so-called extenders. Extenders, i.e. substances that improve oil- and water-repellent effects and likewise enable a reduction of the amounts of the inventive condensation products to be applied, are for example the known emulsions of paraffin-waxes with metal salts and the emulsions of melamine derivative modified by fatty acids prepared according to U.S. Pat. No. 3,506,661 or prepared in a similar manner.

Further possible agents are those which improve flame- or rot-proofing, finishing agents which provide the textile material with the required handle, and others. All these agents are known to the man skilled in the art. In general the usual agents can be used together with the known curing catalysts if required.

An application of the condensation products of the present invention is suitable to all kind of fibrous material. Usual fibrous materials are especially textiles in form of fabrics, knit fabrics or non-wovens and further leather, synthetic leather or paper. The most suitable material to be treated (finished) is textile material. It can be made of natural fibres such as of cellulose or wool, or of synthetic fibres such as of polyesters, polyamides or polyacrylonitriles. Moreover, also textile materials can be treated, of course, which are made of mixtures of natural and synthetic fibres.

The treatment is carried out in known manner. For example, the textiles are padded in an aqueous treatment bath, squeezed to a pick-up of about 60 to 100% by weight, predried for some minutes at 80° to 110° C., especially for 1 to 8 minutes, and cured by heating at about 130° to 170° C. Other application methods such as spraying and kissing are, of course, also suitable and the applied quantities have to be adapted to the corresponding pick-up.

The main advantage of the inventive condensation products consist in the matter of fact that they contain relatively small quantities of perfluorinated alkyl groups, but nevertheless lead to surprisingly high oil-repelling effects in connection with a high degree of water-repelling on fibrous materials and further that these properties can be preserved to a great extent even after several washings and treatments with solvents (dry-cleaning). It could not be expected at all that the described reaction conditions would lead to products that improve the effects to that great extent. Further, the condensation products manufactured according to this invention get their properties, too, from the particular ratio of (A) and (B) used for reacting them.

According to prior art these very good properties could not be expected.

In the following examples the results of the oil-repelling tests are obtained by the method given in AATCC 18-1972. Test of water-repelling is carried out according to DIN 53 888 (a=water-absorption in % by weight, b=water-repellent effect), the spray-test according to AATCC 22-1974, respectively. Dry-cleaning is carried out in a bath ratio of 1:10 (weight of sample to bath volume, solvent:tetrachloroethylene) for 15 minutes. The tetrachloroethylene is renewed for each cleaning process. Washing of samples is carried out by using a heavy duty detergent in a usual machine washing process at temperatures indicated in the examples.

EXAMPLE 1

Manufacture of the condensation product

In a 1 liter 4-neck-flask—equipped with a stirrer, gas inlet tube, internal thermometer and distilling attachment with descending condenser and collecting flask—

233.3 g (about 0.5 mole) of $R_fCH_2CH_2SH$ ($R_f$ comprises 1.3% by weight $C_4F_9-$, 34.3% by weight $C_6F_{13}-$, 31.8% by weight $C_8F_{17}-$, 22.5% by weight $C_{10}F_{21}-$, 8.2% by weight $C_{12}F_{25}-$ and 1.9% by weight $C_{14}F_{29}-$), 39.0 g (about 0.1 mole) of hexamethylol melamine hexamethyl ether and 0.5 g of p-toluene sulphonic acid hydrate are mixed and gradually heated to 115° C. during 30 minutes with stirring and introducing a weakly stream of nitrogen gas and then during further 90 minutes heated up to 175° C. This condition is then kept for further 6 hours while methanol with small quantities of perfluoro compounds distills off.

Thereafter, temperature is decreased to about 80° C. and the yield is fixed bei weighing (95% of the theory). The still warm condensation product is dissolved in 730 g of benzotrifluoride.

Emulsification of the condensation product 500 g of the obtained solution with 25% by weight of condensation product and 1000 g water which contains 2.7% by weight of emulsifier (hydroxyalkylaminopolyglykol ether acetate with 10 moles ethylene oxide in total) are pre-emulsified in a vessel with a high speed stirrer and emulsified by high pressure homogenization at 250 bar and at 50° C. max.). The solvent together with a part of the water are distilled off from the emulsion under reduced pressure obtainable with a water jet vacuum pump at a temperature up to 50° C. and an emulsion is obtained which contains 12.4% by weight of the condensation product.

Oil- and water-repellent finish (A) A polyacrylonitrile fabric (214 g/m²) and (B) a fabric of wool and polyester fibres (65/35; 308 g/m²) are padded to a weight increase of 90 and 70% by weight, respectively, in a bath containing 30 g/l of the above emulsion 10 g/l of an aminoplast resin solution (about 52% by weight of a mixture of dimethylolethylene urea and etherified pentamethylol melamine with methanol, in a ratio of 2.5:1, in aqueous solution)

30 g/l of an extender (about 16% by weight of usual metal salt/paraffin emulsion)

1 ml/l of a catalyst solution (about 75% by weight zinc nitrate hexahydrate solution with small quantities of hydrochloric acid of acetic acid)

30 ml/l of a commercial wetting agent on the basis of isopropanol and isobutanol and 2 ml/l of 60% by weight of acetic acid, dried for 10 minutes at 110° C. and cured by heating for 5 minutes at 150° C.

The obtained effects and their permanence are listed on the following table (a=water absorption in % by weight, b=water repellent effect):

| fabric | washing | Hydrophobic Effects | | | | | |
|---|---|---|---|---|---|---|---|
| | | original | | after 3 washings at 40° C. | | after 3 dry-cleanings | |
| | | a | b | a | b | a | b |
| A | 3 × 40° C. | 11 | 5/5/5 | 8 | 4/4/4 | 8 | 4/4/4 |
| B | 3 × 40° C. | 11 | 5/4/4 | 19 | 4/4/3 | 12 | 4/4/4 |

| | Oil-repellent Effects | | |
|---|---|---|---|
| | original | after 3 washings at 40° C. | after 3 dry-cleanings |
| A | 6 | 6 | 6 |
| B | 6 | 6 | 6 |

For untreated fabrics the following results were obtained:
A: a = 107; b = 1; oil-repellency 0; B: a = 42; b = 1; oil-repellency 0.

EXAMPLE 2

Emulsion A

The emulsion prepared according to Example 1.

Emulsion B

According to the method of Example 1 a condensation product is prepared by using a hexamethylol melamine, highly etherified with ethanol, and as described there used for preparing a stable emulsion (12.5% by weight of condensation product).

Emulsion C

According to Example 2 of U.S. Pat. No. 3,510,455 a condensation product is prepared by using 1 mole of $C_8F_{17}SO_2N(C_2H_5)CH_2CH_2OH$ and 1 mole of hexamethylol melamine hexamethyl ether. An aqueous emulsion of this product is prepared as described in Example 1 (about 12% by weight of condensation product).

Emulsion D

According to column 7, lines 38 ff of U.S. Pat. No. 3,362,782 a condensation product is prepared using 1 mole tetrahydroperfluoroalkyl alcohol (perfluorinated alkyl radical with 7 to 8 C-atoms on average) and 1 mole hexamethylol melamine hexamethyl ether. An aqueous emulsion (about 12% by weight condensation product) is prepared according to Example 1.

Emulsion E

For comparison purposes the compounds mentioned in Example 1 are reacted together in a mole ratio of 1:1 and are used for preparing an aqueous emulsion (about 12% by weight condensation product).

According to the method described in Example 1 a blue cotton twill (222 g/m²) is finished by applying emulsions (A) to (E) each in quantities corresponding to 2.25 g fluorine/liter (30 g/l of emulsion A, 30 g/l of emulsion B, 55 g/l of emulsion D, 48 g/l of emulsion D and 50 g/l of emulsion E), the application bathes containing in addition the following ingredients:

50 g/l of aminoplast resin solution mentioned in Example 1

5 m/l of catalyst solution mentioned in Example 1

2 m/l of 60% by weight acetic acid and 20 g/l of commercial extender (about 20% by weight of a modified melamine ether prepared according to example 1 of U.S. Pat. No. 3,506,661 in emulsion).

The technological tests prove the following values for oil- and water-repellent effects:

| emulsion | | original | | oil-repellency | after 3 dry-cleanings | |
|---|---|---|---|---|---|---|
| | | a | b | | spray-test | oil-repellency |
| (A) | according to the invention | 5 | 5/5/5 | 5 | 3 × 100 | 4 |
| (B) | | 6 | 5/5/5 | 5 | 3 × 100 | 4 |
| (C) | prior art | 32 | 1 | 4 | 3 × 80 | 0 |
| (D) | | 32 | 1 | 4 | 80/70/70 | 0 |
| (E) | for comparison | 29 | 1 | 4 | 80/80/70 | 0 |

-continued

| emulsion | original a | b | oil-repellency | after 3 dry-cleanings spray-test | oil-repellency |
|---|---|---|---|---|---|
| untreated | 103 | 1 | 0 | — | — |

The superiority of the inventively obtained condensation products is clearly proved.

EXAMPLE 3

Manufacture of the condensation product

According to Example 1
0.4 mole (188 g) of $R_fCH_2CH_2SH$ (wherein $R_f$ is for 8.05% by weight $C_6F_{13}$ and for 91.9% by weight $C_8F_{17}$—),
0.1 mole (about 54 g) of hexamethylol melamine etherified to a high degree with n-propanol and
0.5 g oxalic acid
are mixed while stirring and introducing a weak stream of nitrogen gas and heating to 125° C. within 40 minutes and within further 105 minutes up to 185° C. The mixture is kept under these conditions for 5 hours and during this time n-propanol and small quantities of the perfluoro compounds distill off.

Finally it is cooled to 75° C. and the warm condensation product obtained in a yield of 93% of the theory is dissolved in the threefold quantity by weight (608 g) of benzotrifluoride.

Emulsification of the condensation product

According to the procedure described in Example 1 an emulsion is prepared containing 12% by weight of the condensation product by using 150 g of a solution of 10% by weight of a polyvinyl alcohol as emulsifier (polyvinyl alcohol with a saponification number of 140 and a viscosity of 25 mPa.s at 20° C. in a 4% solution) by accordingly reduced quantity of water and removing the solvent under reduced pressure and at up to 45° C.

Oil- and water-repellent finishing

A cotton twill (222 g/m²) is finished with a bath containing 34 g/l of the above emulsion (instead of the emulsion (A) to (E) mentioned in Example 2 besides the products mentioned there and under the conditions mentioned in Example 1 (bath weight increase of 65%) and the following effects have been achieved:

| Hydrophobicity | | | |
|---|---|---|---|
| original | | after 3 machine washings at 60° C. spray-test | after 3 dry-cleanings spray-test |
| a | b | | |
| 5 | 5/5/5 | 3 × 100 | 3 × 100 |

| Oil-Repellency | |
|---|---|
| original | after 3 machine washings at 60° C. spray-test | after 3 dry-cleanings spray-test |
| 4 | 4 | 4 |

In the same manner a condensation product can be prepared by using a hexamethylol melamine etherified with n-butanol to a high extent. If the emulsion that has been manufactured accordingly is applied for finishing of the same fabric, the wash- and dry-cleaning stability will be almost the same.

EXAMPLE 4

Preparation of the condensation products

According to Example 1
(A) 0.35 mole (168 g),
(B) 0.45 mole (216 g), or
(C) 0.6 mole (288 g), respectively, of $R_fCH_2CH_2SH$ (technical mixture, wherein $R_f$ is on average the radical $C_8F_{17}$—) with about 0.1 mole (39 g) of hexamethylol melamine hexamethylether are reacted together; the post-heating period lasts 2 hours only.

After cooling to 75° to 85° C. the yield is determined by re-weighing (95 to 96% of the theory) and by adding 560 g, 685 g, and 885 g, respectively, of benzotrifluoride solutions of 25% by weight are obtained.

Emulsification of the condensation products

The emulsions (A), (B), and (C) are prepared (see Example 1) from the solutions of the condensation products (A), (B), and (C) in the usual manner, the water containing 2% by weight of ethoxylated stearic acid amide (12 mole ethylene oxide per mole of stearic acid amide) (content of condensation product approx. 12.5%).

Oil- and water-repellent finishing

The cotton twill mentioned in Example 3 is padded with the following bath:
(A) 32 g/l of emulsion (A), the other components according to Example 2,
(B) 30 g/l of emulsion (B), the other components according to Example 2,
(C) 28 g/l of emulsion (C), the other components according to Example 2 (weight increase about 65%), dried for 10 minutes at 100° C. and cured for 3 minutes at 160° C.

The resulting effects are listed in the following table:

| emulsion | A | B | C |
|---|---|---|---|
| mole ratio | 1:3,5 | 1:4,5 | 1:6 |
| a | 10 | 7 | 8 |
| b | 5/5/4 | 5/5/5 | 5/5/5 |
| oil-repellency | 5 | 5 | 5 |
| spray-test ⎱ after 3 | 3 × 100 | 3 × 100 | 3 × 80 |
| oil-repellency ⎰ dry cleanings | 5 | 5 | 3 |

For the finishing of a cotton/polyester-overcoat poplin (35/65; 208 g/m²) emulsion B) can be used in the same manner and leads to the following effects after resting in normal climate:

| a | b | oil-repellency (original) | a | b | oil-repellency (after 3 washings at 60° C.) | a | b | oil-repellency (after 3 dry-cleanings) |
|---|---|---|---|---|---|---|---|---|
| 4 | 5/5/5 | 6 | 10 | 4/4/4 | 6 | 16 | 4/3/2 | 6 |

EXAMPLE 5

Manufacture of the condensation product

According to Example 1

233 g (about 0.5 mole) of $R_fCH_2CH_2SH$ (meaning of $R_f$ see Example 1), and 39 g (about 0.1 mole) of hexamethylol melamine hexamethyl ether are reacted under the conditions described there but without post-heating.

In the same manner a reaction with the corresponding perfluoro compound of the formula

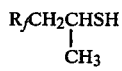

(meaning of $R_f$ see Example 4) can be carried out.

It is also possible to work without nitrogen as protective gas.

After cooling to about 75° C. the yield is determined by re-weighing to 248.3 g (97% of the theory). The still warm condensation product is dissolved in 745 g 1,1,2-trichloro-1,2,2-trifluoroethane.

Emulsification of the condensation product

Emulsification is carried out as described in Example 3 (about 12% condensation product).

Oil- and water-repellent finishing

With a bath containing
30 g/l of the above emulsion
50 g/l of aminoplast resin solution (about 60% by weight of pentamethylol melamine etherified with $CH_3OH$ in aqueous solution)
10 ml/l of catalyst solution (40% by weight of 2-amino-2-methylpropanol hydrochloride in aqueous solution)
2 ml/l of acetic acid 60% by weight and
20 g/l of a commercial extender (see Example 2)
(A) a polyamide taffeta (66 g/m²) and
(B) the blue cotton twill (see Example 2)
are padded (weight increase about 65%), dried for a short time at 105° C. and then cured for 5 minutes at 150° C.

The treated fabrics prove a very good water- and oil-repellency (A: a=7; b=4/4/4, oil-repellency=6; B: =8; b) 5/5/4, oil-repellency=5) and also a good washing- and dry-cleaning permanence.

For all examples the finishing is carried out in an aqueous bath. The percentages refer to % by weight.

We claim:

1. A condensation product obtained by mixing
   (A) 1 mol of hexamethylolmelamine, highly etherified with a $C_1$- to $C_4$-alcohol, with
   (B) 3 to 6 moles of a thiol of the formula $R_f$—X—SH, wherein $R_f$ is perfluoroalkyl of 4 to 14 carbon atoms and X is the divalent radical of ethylene or isopropylene, and allowing compounds (A) and (B) to react over a period of at least about 40 minutes while the reaction temperature is increased to at least 145° C.

2. The condensation product of claim 1, wherein the reaction is carried out by increasing the temperature within 15 to 45 minutes to a temperature of 95° to 130° C. and within a further 25 to 120 minutes to a temperature of 145° to 200° C.

3. The condensation product of claim 2, wherein the temperature of 145° to 200° C. is maintained for a further 2 to 6 hours.

4. The condensation product of claim 1, wherein compounds (A) and (B) are reacted in a mole ratio of 1:(4 to 5.5).

5. In a method of treating fibrous material by applying thereto an aqueous dispersion of a condensation product and curing at increased temperature, the improvement wherein the condensation product is obtained by mixing
   (A) 1 mol of hexamethylol melamine, highly etherified with a $C_1$-$C_4$-alcohol, with
   (B) 3 to 6 moles of a thiol of the formula $R_f$—X—SH, wherein $R_f$ is perfluoroalkyl of 4 to 14 carbon atoms and X is the divalent radical of ethylene or isopropylene, and allowing compounds (A) and (B) to react over a period of at least about 40 minutes while the reaction temperature is increased to at least 145° C.

6. The method of claim 5, wherein the fibrous material is a textile.

7. The condensation product of claim 2, wherein the temperature of 145° to 200° C. is 160° to 180° C.

8. The condensation product of claim 7, wherein the temperature of 160° to 180° C. is maintained for a further 2 to 6 hours.

* * * * *